US007537927B2

(12) United States Patent
Squirrell et al.

(10) Patent No.: US 7,537,927 B2
(45) Date of Patent: *May 26, 2009

(54) REACTION SYSTEM FOR THERMAL CYCLING

(75) Inventors: David James Squirrell, Salisbury (GB); Martin Alan Lee, Salisbury (GB)

(73) Assignee: The Secretary of State for Defence in Her Britannic Majesty's Government of the United Kingdom of Great Britain and Northern Ireland, Wiltshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/782,255

(22) Filed: Jul. 24, 2007

(65) Prior Publication Data

US 2007/0262068 A1 Nov. 15, 2007

Related U.S. Application Data

(63) Continuation of application No. 10/220,970, filed as application No. PCT/GB01/00988 on Mar. 7, 2001, now Pat. No. 7,264,961.

(30) Foreign Application Priority Data

Mar. 8, 2000 (GB) ................................ 0005434.6

(51) Int. Cl.
*C12M 1/00* (2006.01)
*C12M 3/00* (2006.01)

(52) U.S. Cl. .............. 435/303.1; 435/287.2; 435/289.1; 219/388; 165/80.1

(58) Field of Classification Search .............. 435/303.1, 435/287.2, 91.2, 289.1; 219/388; 165/80.1
See application file for complete search history.

(56) References Cited

U.S. PATENT DOCUMENTS

| | | | |
|---|---|---|---|
| 3,556,731 | A | 1/1971 | Martin |
| 4,263,256 | A | 4/1981 | Morle |
| 5,106,538 | A | 4/1992 | Barma et al. |
| 5,106,540 | A | 4/1992 | Barma et al. |
| 5,446,263 | A | 8/1995 | Eigen et al. |
| 5,582,754 | A | 12/1996 | Smith et al. |
| 5,736,314 | A | 4/1998 | Hayes et al. |

(Continued)

FOREIGN PATENT DOCUMENTS

EP 0723812 7/1996

(Continued)

OTHER PUBLICATIONS

Findlay, et al., "Automated Closed-Vessel System for in Vitro Diagnostics Based on Polymerase Chain Reaction", Clinical Chemistry, 39(9): 1927-1933 (1993).

(Continued)

*Primary Examiner*—Walter D Griffin
*Assistant Examiner*—Shanta G Doe
(74) *Attorney, Agent, or Firm*—Kilpatrick Stockton, LLP

(57) ABSTRACT

Method and apparatus for carrying out a thermal cycling reaction, wherein a succession of samples is conveyed through a series of sequentially arranged temperature control sites, each of the sites comprising means for supplying an electric current to, or inducing an electric current in, sample-containing vessels passing through it so as to induce temperature changes in the samples. Also provided is a sample support and its production, the support comprising a succession of sample vessels arranged sequentially one behind the next, preferably in the form of a linked chain, the support comprising an electrically conducting, preferably plastics, material which heats when an electric current passes through it.

25 Claims, 5 Drawing Sheets

U.S. PATENT DOCUMENTS

| | | | | |
|---|---|---|---|---|
| 5,819,842 | A | 10/1998 | Potter et al. | |
| 6,171,850 | B1 * | 1/2001 | Nagle et al. | 435/286.1 |
| 6,312,886 | B1 * | 11/2001 | Lee et al. | 435/4 |
| 6,436,355 | B1 * | 8/2002 | Lee et al. | 422/199 |
| 6,635,471 | B1 | 10/2003 | Lee et al. | |
| 7,264,961 | B2 * | 9/2007 | Squirrell et al. | 435/286.6 |

FOREIGN PATENT DOCUMENTS

| | | | |
|---|---|---|---|
| GB | 2238005 | A | 5/1991 |
| GB | 2254269 | A | 10/1992 |
| GB | 2369592 | A | 6/2002 |
| JP | 09224644 | | 9/1997 |
| WO | WO 83/00296 | | 2/1983 |
| WO | WO 92/13967 | | 8/1992 |
| WO | WO 97/22882 | | 6/1997 |
| WO | WO 98/09728 | | 3/1998 |
| WO | WO 98/24548 | | 6/1998 |

OTHER PUBLICATIONS

"PCR Processor" Research Disclosure, Kenneth Mason Publications, New Hampshire, GB, No. 396, Apr. 1, 1997 pp. 207-211, XP000702403 ISSN: 0374-4353.

Search Report issued in priority Application No. GB 0005434.6.

* cited by examiner

REACTION SYSTEM FOR THERMAL CYCLING

CROSS REFERENCE TO RELATED PATENT APPLICATIONS

The present application is a continuation application of U.S. patent application Ser. No. 10/220,970, now allowed, filed Jan. 10, 2003, now U.S. Pat. No. 7,264,961 which is the national phase of International Application No. PCT/GB01/00988 filed on Mar. 7, 2001 and published in English as International Publication No. WO 01/66254 A1 on Sep. 13, 2001, which application claims priority to Great Britain Application No. 0005434.6 filed on Mar. 8, 2000, the contents of which are incorporated herein by reference.

The present invention relates to methods and apparatus for carrying out thermal cycling reactions, for instance those necessary during an amplification reaction, in particular the polymerase chain reaction (PCR).

Subjecting samples to thermal cycling, as is necessary for the PCR technique, involves a series of discrete and sequential heating and cooling steps, the speed and efficiency of which are limited by the thermal properties of the sample containers. New forms of container with improved thermal conductivity have helped towards solving such problems, but there is still inevitably a time lag during each cycle whilst the container and sample are heated or cooled to the correct temperature.

To improve the overall efficiency of such techniques, it has become customary to "batch process" a plurality of samples at a time, and many forms of reaction unit are available in which an array of samples may be held so as to be subjected together to each processing step.

An alternative apparatus, known as the "Robo-Cycler"™, conveys sample batches between four distinct processing sites in an approximately circular arrangement. Each site is maintained at a different temperature, in order to achieve thermal cycling of the samples. The number of processing steps is limited in this case.

The applicants have devised methods and apparatus, embodiments of which can improve on the speed, efficiency and versatility of such processes and which can facilitate their automation.

According to a first aspect of the present invention there is provided apparatus for carrying out a thermal cycling reaction, the apparatus comprising a series of sequentially arranged temperature control sites and conveyor means for conveying a succession of samples through them, each of the sites comprising means for supplying an electric current to, or inducing an electric current in, a sample-containing vessel passing through them so as to induce temperature changes in the sample.

The use of an electric current to cause a temperature change in a sample can preferably be achieved by incorporating into a vessel containing the sample an element formed from an electrically conducting material which heats when electric current passes through it. This allows the sample temperature to be readily controlled, ideally separately from that of adjacent samples in the succession, by a series of relatively simple electrical sources located at the temperature control sites of the apparatus. Such sources are generally less cumbersome than conventional heating means such as heating blocks, and a large number of them can more easily be arranged in a desired sequence for the succession of samples to pass through. Each sample effectively carries its own heating means with it; the temperature control sites need only provide an appropriate source of electrical power and associated controls. At each site an appropriate current may be applied to achieve a desired temperature change, following which the sample may progress to another site at which a different current may be applied, whilst an adjacent sample in the succession is being subjected, separately, to a similar sequence of thermal changes.

Thus, typically, temperature changes may be induced in a sample by moving it between successive temperature control sites. This means that the apparatus of the invention is particularly well suited to the sequential, effectively continuous, processing of any desired number of samples. It is also well suited to automation, the main controls necessary to effect thermal cycling being over the conveyor means and the electrical current sources at the temperature control sites.

In the context of the present invention, a "continuous" method means one which is continuous throughout its duration, as opposed to a purely batch method. In practice the apparatus can be used to process a relatively large number of samples in continuous succession (in other words, by a "semi-batch" process).

Thus, instead of (as in the prior art) a batch of samples being either (a) heated or cooled at a first site and then conveyed together to a second site for another heating or cooling step, or (b) thermally cycled as a stationary batch at a single location, all samples can be moved successively through each such site, suitably in the form of a "chain" of samples progressing sequentially one behind the other. Ideally, each sample reaches a particular temperature control site at a different time to its adjacent sample(s) in the succession. Each may therefore be processed separately from (for instance, it may at any given time be at a different temperature to) its adjacent sample(s).

The succession of samples which can be processed using the apparatus is preferably linear, or substantially so, in arrangement, or at least non-circular. The conveyor means may be arranged so as to convey the samples continuously through the temperature control sites, again preferably in a linear fashion, and is preferably operable automatically or at least partially so.

The temperature control sites of the apparatus are preferably also arranged in a linear succession, although they need not be in a straight line. There are preferably more than 4 of them, more preferably more than 6, most preferably more than 10 or 16 or 20 or 50 or 100. Typically the apparatus may include up to 100, 150 or 200 temperature control sites.

At the temperature control sites, conventional equipment may be used to cause the necessary electrical effect. Current may be supplied, for instance, via appropriately positioned electrical contacts which can contact complementary parts of a sample vessel as it passes through the site. These contacts may be incorporated in the conveyor means (for instance, a series of rollers) by which the samples are driven through the temperature control sites. Alternatively, a magnetic field may be used at a site to induce an electric current in a sample vessel.

Each such site may be maintained to supply or induce a constant level of current in all sample vessels passing through it. This simplifies operation, whilst still allowing thermal cycling of each individual sample as it progresses between sites.

The apparatus may additionally comprise control means, preferably automatable, by which the supply of current at the temperature control sites, and/or the temperature of the samples, may be monitored and/or controlled. Conventional equipment may be used to perform such tasks.

The apparatus may comprise additional processing sites having equipment suitable for processing steps such as sample or reagent loading or sample monitoring. At some of these processing sites, conventional apparatus such as heating blocks, ovens, fluid baths, hot air blowers, fans and the like may, although this is not normally necessary, be used to provide additional heating and/or cooling steps for samples passing through.

One or more of the additional processing sites may be for monitoring the composition of samples passing through the site and/or the progress of reactions occurring in the samples, for example by monitoring the nature and/or level of a target amplification product in the samples. Reagents in the samples may be labelled for instance with coloured or fluorescent labels, the presence of which may be detected at a monitoring site by the application of suitable radiation. In such cases each sample may be contained in a vessel at least a portion of which is transparent or translucent, to allow any applied radiation to reach the samples and their condition to be appropriately monitored. In this context, “transparent” and “translucent” mean in respect to any detectable signal by which the properties of a sample may be monitored—such signals include, for instance, visible or ultraviolet light, fluorescence and radioactivity.

Conventional detection apparatus may be used at a monitoring site to recognise detectable signals emitted from samples. Such detection apparatus may for instance comprise means for detecting the absorption or emission of radiation (eg, visible or ultraviolet light, fluorescence, radioactivity) by a sample, and/or means for stimulating such emission, examples being light meters or luminometers. Reaction monitoring can be efficient, accurate and continuous throughout the reaction, and samples can be monitored individually as they pass through the monitoring site.

Other functions may be carried out at the additional processing sites. For example, sample vessels may be loaded with desired reagents at a loading site, and sealed shut at a downstream site. There may also be sample preparation and/or processing sites, for instance washing stations or sites at which further samples or reagents are introduced into sample vessels.

The conveyor means of the apparatus may comprise conventional means such as rollers, tracks and conveyor belts, the exact form depending on the number and nature of the samples and the way in which they are arranged and supported. The samples can suitably be contained in vessels such as those described in WO-98/24548, which comprise electrically conducting materials (in particular polymers) that heat when an electric current passes through them. Current may then be supplied to, or induced in, the vessels as they pass through a site, so as to cause a desired temperature change.

However, when using the apparatus of the invention, the samples are preferably provided on or in a (preferably elongate) sample support which comprises a succession of separate sample vessels arranged sequentially one behind the next and is adapted to be conveyed continuously through a series of processing sites, the support comprising an electrically conducting material which heats when an electric current passes through it.

The sample vessels are preferably separate from one another and individually sealable and/or isolatable. They may be provided on or in the support in a linear, or substantially linear, arrangement, or at least in a non-circular arrangement. The support may thus preferably be used to allow each sample vessel to reach a given processing (which includes temperature control) site at a different time to its adjacent vessel(s) in the succession, and each vessel may at any given time occupy a different site, and/or be held at a different temperature, to its adjacent vessel(s). The support should be continuous over the area supporting the sample vessels.

A second aspect of the invention provides such a sample support, for use with apparatus according to the first aspect.

The electrically conducting material of the support may be a metal such as aluminum or copper but is preferably a plastics material. Electrically conducting polymers, for use in this way, are known in the art and may be obtained for example from Caliente Systems Inc. of Newark, USA. Other examples of such polymers are disclosed for instance in U.S. Pat. Nos. 5,106,540 and 5,106,538. Suitable conducting polymers can provide temperatures of up to 300° C., ideal for use in PCR processes.

The electrically conducting plastics material may in particular be a polymer loaded with an electrically conducting material. Such conductor-loaded materials are available for instance from the French company RTP. A polymer, typically a thermosetting polymer resin such as a polyethylene, polypropylene, polycarbonate or nylon polymer, may contain embedded in it elements of an electrically conducting material such as carbon (usually in the form of fibres) or a metal (copper, for example). These elements may constitute between say 1 and 50% w/w or higher of the electrically conducting plastics material.

An advantage of such polymers is their ability to heat rapidly. The heating rate depends upon the precise nature of the polymer, its dimensions and the amount of current applied. Preferably the polymer has a high resistivity for example in excess of 1000 ohm.cm. Its temperature can be readily controlled by controlling the amount of electric current passing through it, allowing it to be held at a desired temperature for a desired period of time. The transition rate between temperatures can similarly be controlled. Moreover, relatively rapid cooling can also be assured because of the low thermal mass of the polymer.

The use of such polymers in the construction of sample vessels, for instance for PCR processing, is described in WO-98/24548. The polymers may be injection moulded and may therefore be used directly to form sample vessels and their parts. Thus, in a sample support according to the invention, an electrically conducting material, preferably plastics, may form part of or be integral with each sample vessel. Suitably, a sample vessel or support may be made from another polymer such as polypropylene which may be moulded with the conducting polymer, allowing the vessel or support to incorporate separate elements of the conducting polymer in desired locations. For example, each sample vessel ideally incorporates one or more electrically conducting element(s) which are separate from those of adjacent vessels, to allow individual temperature control for each vessel.

Alternatively the support, incorporating the sample vessels, may be formed from (for instance by injection moulding or extrusion), or include a layer of, an electrically conducting material. In this case the support preferably comprises a succession of electrically isolatable regions corresponding to the positions of individual sample vessels, again to allow for independent temperature control. This can be achieved for instance by providing appropriately positioned electrically insulating elements (which may include apertures) in the support. Alternatively the provision of a separate electrode pair for each sample vessel may allow the supply of a localised current to each such vessel.

As a yet further alternative (again as described in WO-98/24548), an internal surface of each sample vessel may be coated with the conducting material, for example by a lamination and/or deposition technique. A conducting plastics material may suitably be provided in the form of a sheet material or film, for example of from 0.01 to 10 mm, preferably from 0.1 to 0.3 mm, thick. A metal conductor may be provided in the form of a foil or an electrolytically deposited coating of similar thickness.

In another alternative, an electrically conducting element is provided in close proximity to, ideally in contact with, each sample vessel. Suitable arrangements include a sheath of a conducting material around the sample vessel. Again, the material is preferably an electrically conducting polymer.

Electrically conducting plastics materials of the type described above tend to emit heat when electric current passes through them, and so may be used to cause a local temperature change in samples with which they come into contact.

The use of electrically conducting materials, in particular plastics materials, in accordance with the present invention allows a large number of sample-containing vessels to be processed sequentially and effectively continuously, since each vessel may be separately supplied with electric current so as independently to control the temperature of the sample it contains. At the same time, the incorporation of such temperature control means into the fabric of the vessel itself can allow relatively simple and compact sample supports and processing apparatus to be achieved.

All manner of conventional reaction vessels may be linked together appropriately, or produced in continuous form, to provide a sample support of use in the apparatus of the present invention. Sample vessels in the form of reaction wells may be formed in for instance a flexible strip by pressing or moulding.

Thus, a sample support according to the invention may comprise a strip of a suitably flexible (preferably plastics) material, on which a succession of sample vessels is mounted or in which a succession of such vessels is formed. The flexible strip may itself be formed from, or incorporate (for instance as a laminate) an electrically conducting material as described above.

More preferably, however, the sample support comprises a series of reaction "units", each of which provides one or more sample vessels, and which are preferably linked together as a chain so as to be conveyable sequentially through processing sites. Examples of such reaction units, although not in linked form, are described for instance in WO-98/09728 and by Findlay et al in "Automated Closed-Vessel System for in Vitro Diagnostics Based on Polymerase Chain Reaction", *Clinical Chemistry,* 39, no. 9, 1993, pp 1927-1933.

It is possible to utilise a linked chain of reaction vessels or units because the means for heating each of them (the electrically conducting material) allows more selective and localised heating of individual samples, even those which are adjacent one another in the succession. In turn, the ability to link a succession of sample vessels or reaction units can greatly increase processing efficiency, reduce the size and complexity of processing apparatus and facilitate automation.

Each reaction unit may for example have the approximate size and shape of a credit card. The units may be mounted on the sample support or, conveniently, they may be produced in the form of a chain of linked units, the chain ideally having sufficient flexibility to be stored as a roll or as a fanned stack. Prior art reaction systems would have batch processed such units (as described by Findlay et al, supra), or would have thermally cycled each unit whilst keeping it stationary at a single processing site; the present invention allows the units to be processed continuously, as produced.

The sample support of the invention preferably comprises more than three or more than five sequentially arranged sample vessels, more preferably ten or more, most preferably at least twenty or fifty or a hundred or more. The vessels may be arranged in an array, for instance in pairs or in larger groups, so that for instance two adjacent vessels reach a processing site simultaneously, another two following behind and another two behind them, etc. Suitably the vessels are in the form of capillary tubes.

Preferably at least a portion of each vessel is transparent or translucent to assist in the monitoring of a sample contained in it.

The sample support preferably comprises electrical contacts (for instance, at an edge of the support, and/or provided in each sample vessel or reaction unit) to facilitate the supply of current to the electrically conducting material as the support passes through an appropriate processing site. Alternatively, an electric current may be induced in the conducting material for example by exposing it, in use, to suitable electrical or magnetic fields. Ideally the support and sample vessels are arranged so that each vessel or at least a set of vessels, may be individually supplied with current, allowing its temperature to be controlled independently of other vessels on the support.

The vessels of the sample support, and/or reaction units containing them, may be labelled to identify them during processing, for instance with microchips holding relevant information. The vessels may be pre-loaded with one or more reagents, in particular freeze dried, frozen or stabilised reagents, in conventional fashion. Alternatively reagents may be dispensed into the vessels at an in-line pipetting station provided in apparatus according to the invention.

The sample support, and/or each of the sample vessels or reaction units it comprises, is preferably designed to be disposable after use.

The support may comprise an electrically conducting layer and a facing layer with one or more reagent wells defined between them, as described for instance (although not in continuous form) in co-pending UK patent application number 9922971.8. Such sample vessels may be filled with appropriate reagents and then sealed prior to undergoing thermal cycling.

Using apparatus according to the first aspect of the invention, sample vessels on a support according to the second aspect may be filled and/or sealed at processing sites upstream of the temperature control sites and optional monitoring sites. As with other aspects of the use of the apparatus, these steps may be partially or fully automated.

Apparatus according to the invention may therefore comprise, upstream of the temperature control sites, means for loading reagents into a succession of sample vessels, preferably provided on or in a sample support, and/or means for sealing loaded sample vessels. It also preferably comprises means for producing a sample support of the type described above and means for conveying the so-produced sample support to downstream processing sites.

A third aspect of the present invention provides a method for carrying out a thermal cycling reaction, which involves using apparatus according to the first aspect, and/or a sample support according to the second, to convey a succession of samples through a series of sequentially arranged temperature control sites, at each of which sites an electric current is supplied to, or induced in, a sample-containing vessel passing through them so as to induce temperature changes in the sample.

In such a method, the samples are preferably conveyed continuously through the temperature control sites. The thermal cycling reaction is suitably part of an amplification reaction, in particular a PCR reaction.

The method is preferably at least partially automated, for instance under computer control. It can enable high throughput testing, which is especially desirable for diagnostic methods such as the DNA amplification of pathogens or other contaminants (including genetic pollution) in for instance the air, body fluids, foodstuffs and the like.

The method may be particularly useful in the online monitoring of environmental conditions, for instance in a storage atmosphere, a reaction mixture, a water or food supply, a manufactured product or by-product, a waste outlet or even in body fluids in vivo.

Samples may be continually extracted from the environment of interest and subjected successively, using the method of the invention, to a diagnostic process involving thermal cycling. As the samples pass through monitoring sites, time-dependent profiles of their composition may be acquired.

At one or more additional processing sites, samples may accordingly be acquired, and/or loaded into vessels and/or monitored, as described above in connection with the apparatus of the invention.

According to a fourth aspect, the present invention provides a method for producing a sample support according to the second aspect, the method comprising forming (for instance by pressing) a succession of reaction wells in a flexible strip comprising an electrically conducting (preferably plastics) material which heats when an electric current passes through it. This method may include providing one or more of the reaction wells with one or more appropriately positioned electrical contacts. It may also include pre-loading one or more of the reaction wells with a desired reagent or reagents.

Again, the flexible strip may be made of an electrically conducting material, or it may incorporate a layer of such a material.

The method of the fourth aspect of the invention may be incorporated into that of the third aspect.

According to fifth and sixth aspects of the invention, there are provided (a) apparatus according to the first aspect in combination with a sample support according to the second aspect, and (b) the use of a sample support according to the second aspect in a method according to the third.

The present invention will now be described in more detail with reference to the accompanying illustrative drawings, of which:

All drawings are schematic.

Figures 1, 2, 3:
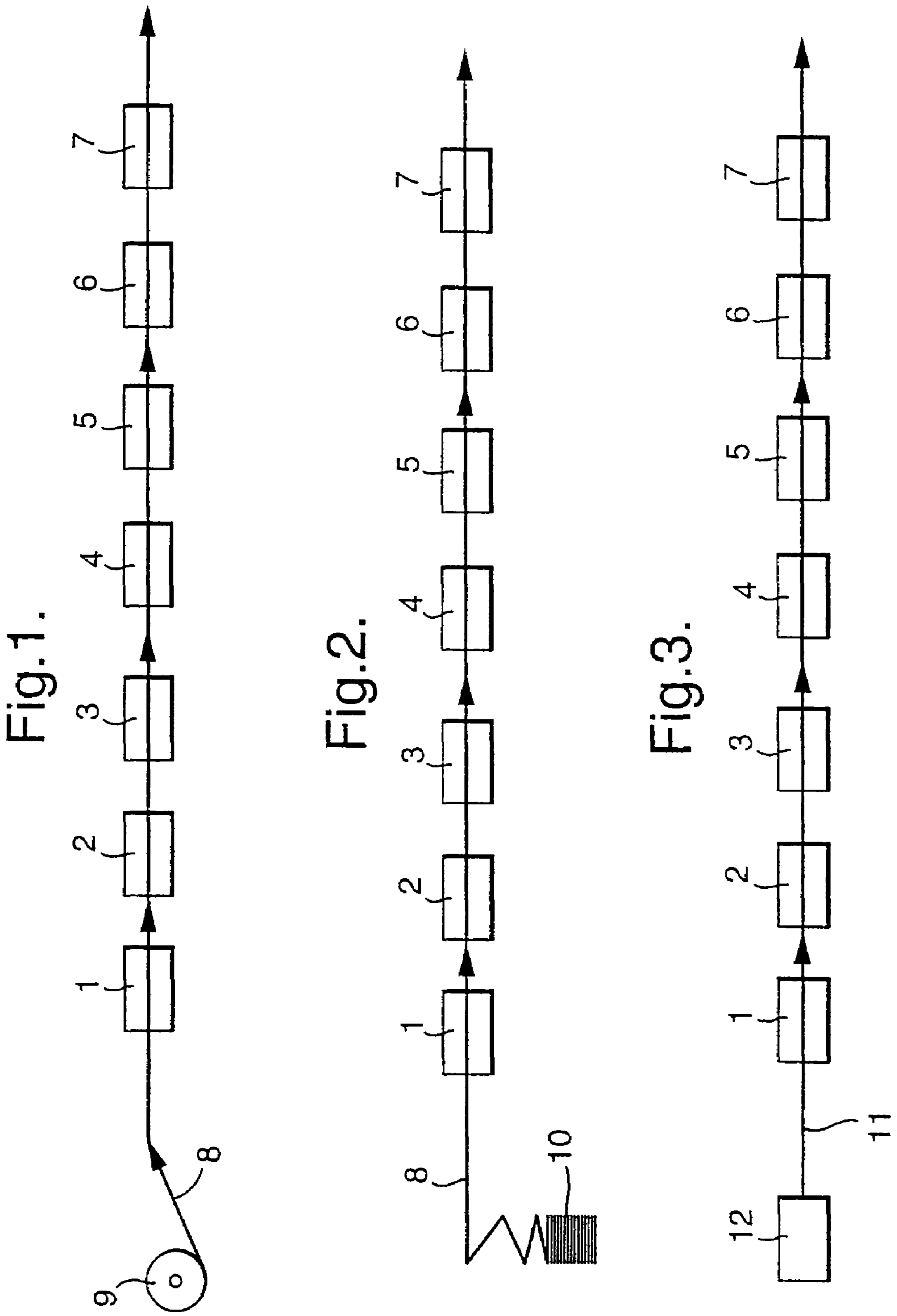
FIG. 1 illustrates a method and apparatus in accordance with the invention.
FIGS. 2 and 3 illustrate alternative methods and apparatus according to the invention.

Referring firstly to FIG. 1, the method illustrated involves conveying a succession of samples, on a continuous support, through a series of sequentially arranged processing sites 1-7 in the direction shown by the arrows. In this case sites 3-6 are temperature control sites at which the samples are thermally cycled between desired temperatures. The additional processing sites are for (1) loading samples into sample vessels, (2) sealing the open ends of the vessels and (7) monitoring the progress of reactions in the samples, and/or the sample composition (for instance in an assay for detecting a target material in the sample) by irradiating the samples and detecting light emitted by appropriately labelled reagents. [Alternatively one or more complete thermal cycles of heating and cooling can be carried out at any of sites 3, 4, 5 and/or 6]. Conventional apparatus, preferably automated, is used at the seven sites to effect the necessary processing steps.

Typically, apparatus according to the invention may comprise many more processing sites than the seven shown schematically in FIG. 1. For instance, it may comprise 150 or more temperature control sites in order to carry out a typical PCR reaction of three or more steps.

Figure 4:
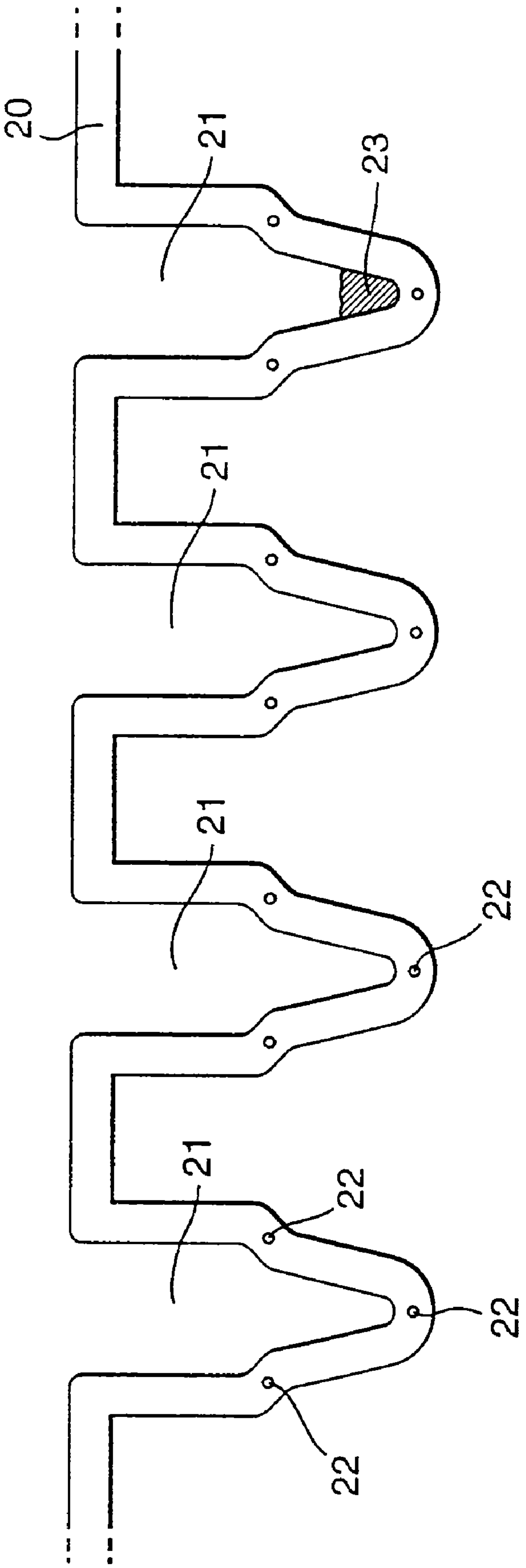
FIGS. 4 and 5 are vertical longitudinal sections through sample supports for use in the methods and apparatus of FIG. 1, 2 or 3.

In the FIG. 1 system, the samples are contained in disposable reaction units of the general form disclosed in for instance WO-98/09728, or by Findlay et al (supra), or in co-pending UK patent application number 9922971.8 (see FIG. 4). Each unit provides an array of reaction "wells", which can be loaded at site 1 with the desired reagents and sealed shut at site 2. A continuous chain 8 of such units, linked together by flexible plastics "bridges", is stored on a roll 9 and from there is fed through the processing sites 1-7. Conventional drive means (not shown) are used to move the chain 8 through the apparatus automatically.

The FIG. 2 system is identical to that of FIG. 1, except that the chain 8 of reaction units is stored as a fanned stack 10.

In the alternative system of FIG. 3, a chain 111 of reaction units is manufactured at an additional site 12 upstream of the processing sites 1-7, and from thence fed directly through the apparatus to allow the desired thermal cycling reactions to take place.

Figure 5:
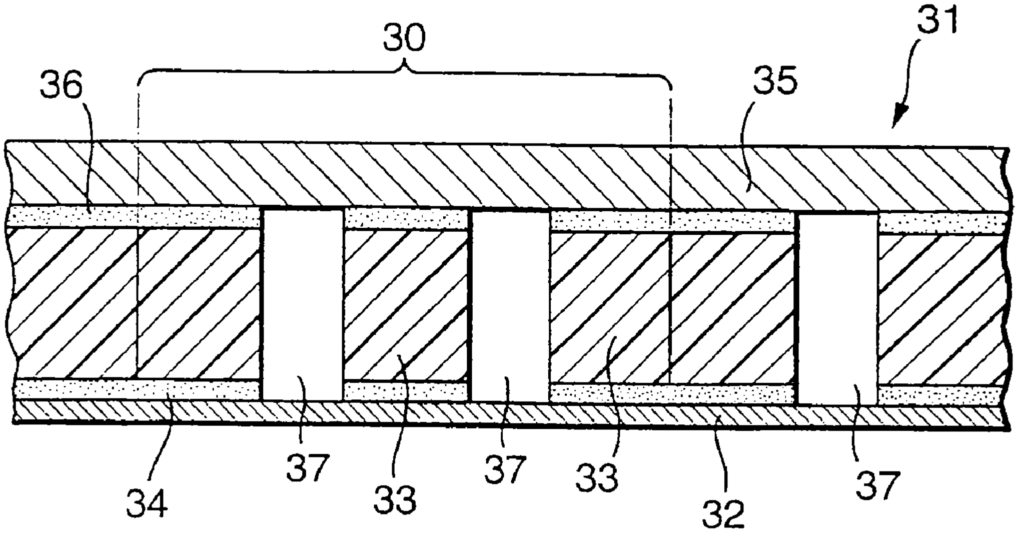

Sample supports of use in the FIGS. 1, 2 and 3 systems are shown in FIGS. 4 and 5. That of FIG. 4 is in the form of an elongate flexible strip 20 in which a succession of generally tubular sample wells 21 has been punched using a conventional die and tube former. The strip is made from an electrically conducting polymer, of the type described above, which heats when electric current passes through it. Each sample well is provided with electrical contacts 22 to enable current to be supplied to it at appropriate stages in processing. The wells may be pre-loaded with for instance dried or frozen reagents, as shown at 23.

A method in accordance with the invention may include the steps of punching out the sample wells 21 in a blank polymer strip, introducing the electrical contacts 22, loading the desired reagents into the wells, sealing the loaded wells shut (for instance, by heat sealing, or by means of an adhesive or plug) and then conveying the thus-formed succession of samples through a series of temperature control sites and optional additional processing sites such as monitoring sites. Thus the entire process may be conducted continuously, and lends itself well to complete automation.

Figure 6:
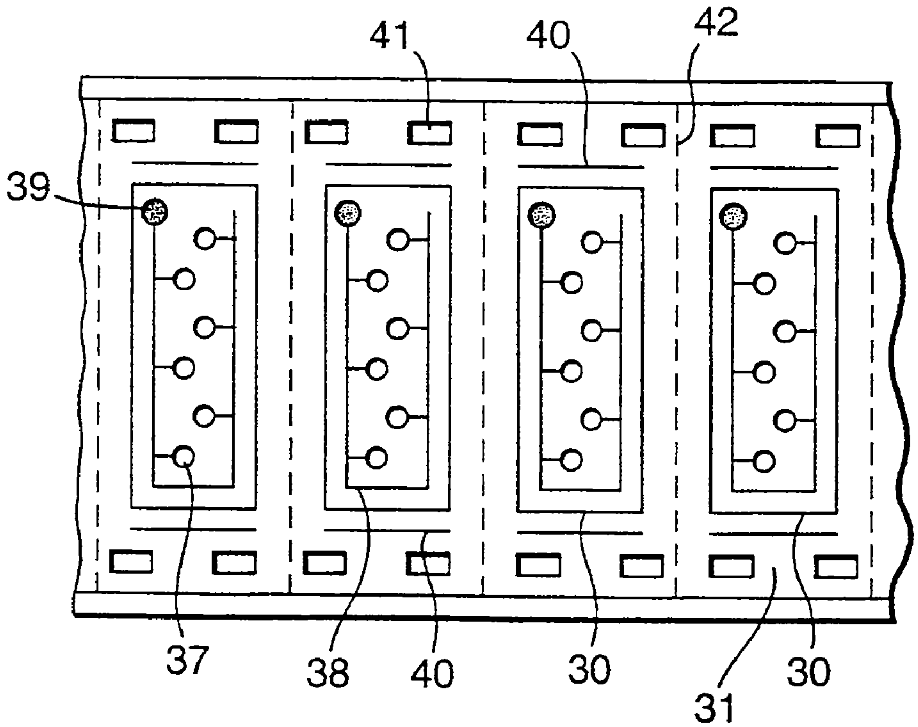
FIG. 6 is a horizontal section through the sample support of FIG. 5.

The FIGS. 5 and 6 sample support comprises a series of approximately credit card sized reaction "units" 30 provided in a flexible strip generally labelled 31. The strip comprises a thin aluminum foil backing layer 32, a polycarbonate spacing layer 33 adhered to the backing layer by an adhesive layer 34 and an optically transparent polycarbonate facing layer 35 adhered to the spacing layer by adhesive 36. In each unit, the spacing layer 33 is provided with an array of holes 37 (in this case, six) which define sample wells. The holes 37 communicate with a channel 38 and an inlet 39 (see FIG. 6; omitted from FIG. 5 for clarity) through which reagents may be introduced into the sample wells. The inlet is sealed shut prior to carrying out thermal cycling reactions on the enclosed samples. Loading and sealing may be effected by methods described in for instance WO-98/09728, Findlay et al (supra), or co-pending UK patent application number 9922971.8.

The presence of the thermally conductive aluminum layer 32 reduces the time needed to heat or cool samples in the unit to desired temperatures. Electrodes 40 are provided on the strip 31 adjacent each "unit" (see FIG. 6).

There may be any number of sample wells provided in each unit, arranged in any appropriate manner. The wells may be pre-loaded with desired reagents.

The strip 31 is provided with a regularly spaced succession of engageable driving means, in this case sprocket holes 41 (FIG. 6), via which it may be driven through a succession of processing sites. It is scored along the lines 42 between adjacent units, to increase its flexibility.

Alternative sample supports in accordance with the invention may comprise a flexible backing strip corresponding for instance to the foil backing layer 32 of FIGS. 5 and 6, onto which is mounted a series of reaction units incorporating the facing and spacing layers 35 and 33. The backing strip could be made of any electrically conducting material, in particular an electrically conducting polymer.

As a further alternative, the conducting layer may be omitted and instead electrically conducting elements incorporated separately into each sample well. These could take the form of appropriately placed regions of an electrically conducting polymer.

Figure 7:
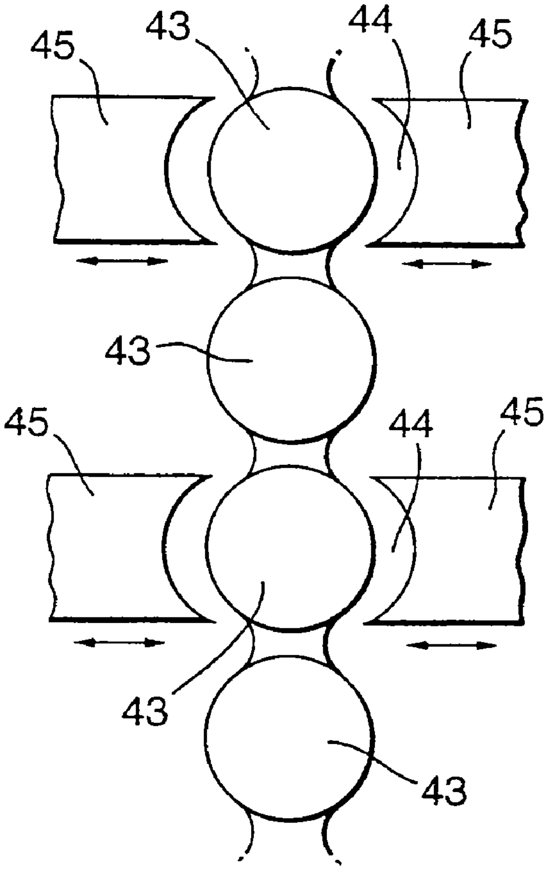
FIG. 7 is a plan view of a sample support passing through apparatus in accordance with the invention.

FIG. 7 illustrates how a chain of individual PCR reaction vessels (tubes 43), linked together in any appropriate manner, may be conveyed through a series of processing sites 44 in accordance with the present invention. At each site a pair of moveable actuators 45 is arranged to apply a magnetic field to, and hence induce a current in, conducting elements present in the tubes as they pass through the site.

Figure 8:
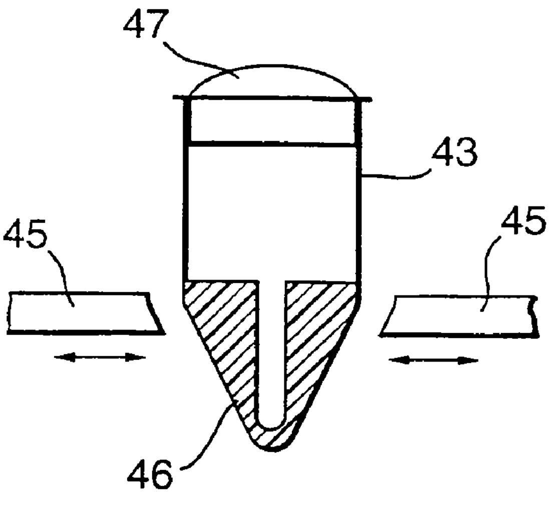
FIG. 8 is a vertical section through the FIG. 7 arrangement.

Each tube 43 (see FIG. 8) is a two-part injection moulding formed primarily from polypropylene but incorporating a shaped outer layer 46 of an electrically conducting polymer. This outer layer heats when current is induced in it by the actuators 45, thus supplying heat to the contents of the tube.

The tube 43 also has a plug 47 by which its open end is sealed after sample loading.

Figure 9:
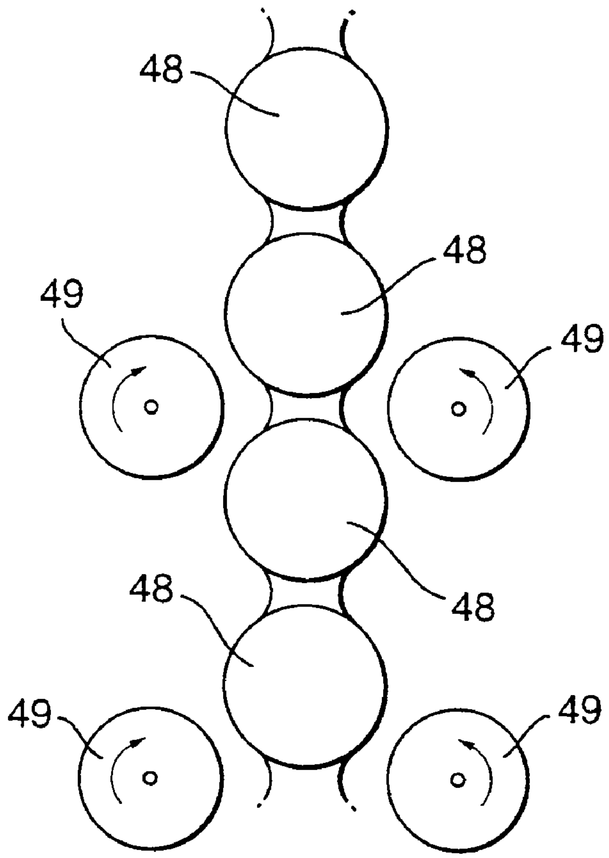
FIGS. 9 and 10 are a plan view and vertical section respectively of a sample support passing through an alternative apparatus according to the invention.
Figure 10:
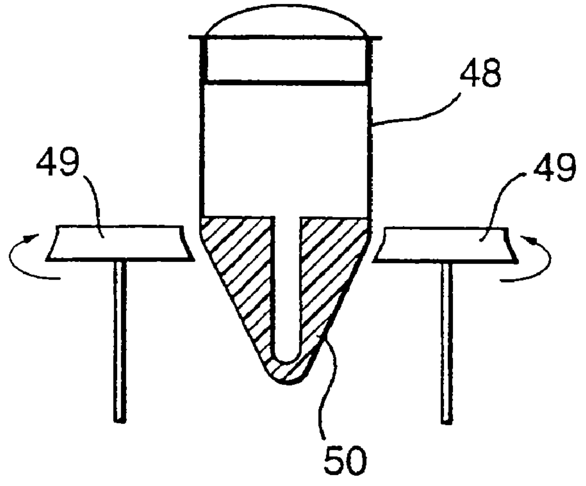

In the alternative system illustrated in FIGS. 9 and 10, a chain of PCR tubes 48 is conveyed through apparatus according to the invention by pairs of "pinch rollers" 49. The rollers are made of an electrically conducting material such as steel and are mounted so that, in use, they form an electrical contact with a conducting polymer outer layer 50 (see FIG. 10) of each tube as it passes them. This contact may be via appropriately positioned brushes or the like, not shown in the figures.

The invention claimed is:

1. A sample support for use with an apparatus for carrying out a thermal cycling reaction, the apparatus comprising a series of sequentially arranged temperature control sites and conveyor means for conveying a succession of samples through them, each of the sites comprising means for supplying an electric current to, or inducing an electric current in, a sample-containing vessel passing through them so as to induce temperature changes in the sample, the support comprising a succession of sample vessels arranged sequentially one behind the next which are linked together as a chain so as to be conveyable sequentially through a series of processing sites, the support comprising an electrically conducting material that heats when an electric current passes through it.

2. The sample support of claim 1, wherein each sample vessel incorporates a separate element made from an electrically conducting material that emits heat when an electric current passes through it.

3. The sample support of claim 1, wherein the electrically conducting material is a plastics material.

4. The sample support of claim 3, wherein the electrically conducting plastics material is a polymer loaded with an electrically conducting material.

5. The sample support of claim 4, wherein the electrically conducting material is either carbon or a metal.

6. The sample support of claim 1, wherein the sample vessels are in a linear, or substantially linear, arrangement.

7. The sample support of claim 1, comprising a strip of a flexible material, on which a succession of sample vessels is mounted or in which a succession of sample vessels is formed.

8. The sample support of claim 7, wherein the flexible material is an electrically conducting plastics material.

9. The sample support of claim 7, wherein the flexible material incorporates a layer of an electrically conducting plastics material.

10. The sample support of claim 1, comprising a succession of electrically isolatable regions corresponding to the positions of individual sample vessels, to allow for independent temperature control for each of the vessels.

11. The sample support of claim 7, wherein the sample vessels are formed in the flexible material.

12. The sample support of claim 1, which is designed to be disposable after use, or wherein the sample vessels or reaction units that it comprises are designed to be disposable after use.

13. The sample support of claim 1, further comprising electrical contacts to facilitate the supply of electric current to the conducting material as the support passes through an appropriate processing site.

14. The sample support of claim 1, wherein at least a portion of each sample vessel is transparent or translucent, so as to allow monitoring of the composition of a sample contained in the vessel and/or the progress of a reaction occurring in the sample.

15. The sample support of claim 1, comprising more than three sequentially arranged sample vessels.

16. The sample support of claim 15, comprising ten or more sequentially arranged sample vessels.

17. The sample support of claim 1, wherein the sample vessels are arranged in an array.

18. A sample support of claim 1, wherein one or more of the sample vessels is pre-loaded with one or more reagents.

19. The sample support of claim 1, in the form of a roll.

20. The sample support of claim 1, in the form of a fanned stack.

21. The sample support of claim 1, further comprising engageable driving means by which it may be driven through a succession of processing sites.

22. A method for producing the sample support of claim 1, the method comprising forming a succession of reaction wells in a flexible strip comprising an electrically conducting material that heats when an electric current passes through the material.

23. The method of claim 22, wherein the electrically conducting material is a plastics material.

24. The method of claim 22, wherein one or more of the reaction wells comprise one or more electrical contacts.

25. The method of claim 22, further comprising pre-loading one or more of the reaction wells with a reagent or reagents.

* * * * *